United States Patent
Inoue et al.

(10) Patent No.: US 10,918,536 B2
(45) Date of Patent: Feb. 16, 2021

(54) DISPOSABLE WEARING ARTICLE

(71) Applicant: UNICHARM CORPORATION, Shikokuchuo (JP)

(72) Inventors: Takuya Inoue, Kanonji (JP); Shunsuke Takino, Kanonji (JP); Hideaki Maki, Kanonji (JP)

(73) Assignee: UNICHARM CORPORATION, Ehime (JP)

(*) Notice: Subject to any disclaimer, the term of this patent is extended or adjusted under 35 U.S.C. 154(b) by 311 days.

(21) Appl. No.: 16/063,328

(22) PCT Filed: Aug. 19, 2016

(86) PCT No.: PCT/JP2016/074173
§ 371 (c)(1),
(2) Date: Jun. 18, 2018

(87) PCT Pub. No.: WO2017/115492
PCT Pub. Date: Jul. 6, 2017

(65) Prior Publication Data
US 2018/0360673 A1  Dec. 20, 2018

(30) Foreign Application Priority Data

Dec. 28, 2015 (JP) ................................. 2015-257242

(51) Int. Cl.
| | |
|---|---|
| *A61F 13/49* | (2006.01) |
| *A61F 13/494* | (2006.01) |
| *A61F 13/495* | (2006.01) |
| *A61F 13/496* | (2006.01) |
| *A61F 13/551* | (2006.01) |
| *A61F 13/58* | (2006.01) |

(52) U.S. Cl.
CPC .......... *A61F 13/495* (2013.01); *A61F 13/496* (2013.01); *A61F 13/49007* (2013.01);
(Continued)

(58) Field of Classification Search
CPC .......... A61F 13/49007; A61F 13/49466; A61F 13/495; A61F 13/496; A61F 13/58;
(Continued)

(56) References Cited

U.S. PATENT DOCUMENTS

| | | | | |
|---|---|---|---|---|
| 5,904,675 A | * | 5/1999 | Laux | A61F 13/49009 604/385.29 |
| 6,280,426 B1 | * | 8/2001 | Turner | A61F 13/49466 604/385.01 |

(Continued)

FOREIGN PATENT DOCUMENTS

| | | |
|---|---|---|
| JP | 2001-252303 A | 9/2001 |
| JP | 2004-141641 A | 5/2004 |

(Continued)

OTHER PUBLICATIONS

International Search Report in PCT Application No. PCT/JP2016/074173, dated Nov. 15, 2016, 4pp.

*Primary Examiner* — Catharine L Anderson
*Assistant Examiner* — Lynne Anderson
(74) *Attorney, Agent, or Firm* — Hauptman Ham, LLP

(57) ABSTRACT

A diaper has vertical and lateral directions, and a skin facing surface and a non-skin facing surface on an opposite side thereof, includes a front waist region, a rear waist region, a crotch region positioned between the front and rear waist regions, and includes a pair of leg openings, and a waist opening defined by side edges of the front and rear waist regions. At least one of the front and rear waist regions includes a pair of tape fasteners fixed to the non-skin facing surface of the side edges. At least one of the front and rear waist regions includes a pocket openable toward the crotch region, on the skin facing surface. An upper end of a fixing part of the tape fastener is positioned at a lower side of a closing edge (folding part) positioned on the waist opening side of the pocket in the vertical direction.

5 Claims, 15 Drawing Sheets

(52) U.S. Cl.
CPC ........ *A61F 13/551* (2013.01); *A61F 13/5512* (2013.01); *A61F 13/58* (2013.01); *A61F 13/49466* (2013.01); *A61F 2013/49493* (2013.01); *A61F 2013/55125* (2013.01)

(58) Field of Classification Search
CPC .... A61F 2013/49493; A61F 2013/5666; A61F 2013/586; A61F 2013/587; A61F 2013/588
See application file for complete search history.

(56) References Cited

U.S. PATENT DOCUMENTS

| | | | |
|---|---|---|---|
| 6,336,922 B1 * | 1/2002 | VanGompel | A61F 13/49011 604/385.29 |
| 6,605,185 B2 * | 8/2003 | Sasaki | D21F 5/028 162/198 |
| 2003/0045853 A1 * | 3/2003 | Sauer | A61F 13/495 604/385.19 |
| 2003/0050616 A1 * | 3/2003 | Reynolds | A61F 13/49466 604/369 |
| 2005/0131378 A1 | 6/2005 | Sasaki et al. | |

FOREIGN PATENT DOCUMENTS

| | | |
|---|---|---|
| JP | 2015-134021 A | 7/2015 |
| JP | 5832619 B1 | 12/2015 |
| WO | 2015/107767 A1 | 7/2015 |
| WO | 2016/051937 A1 | 4/2016 |

* cited by examiner

DISPOSABLE WEARING ARTICLE

RELATED APPLICATIONS

The present application is a National Phase of PCT/JP2016/074173, filed Aug. 19, 2016 which claims priority to Japanese Patent Application No. 2015-257242, filed Dec. 28, 2015.

TECHNICAL FIELD

The present disclosure relates to a disposable wearing article.

BACKGROUND

Conventionally, disposable diapers provided with a pocket for collecting and containing body exudates are known. For instance, Patent Literature 1 discloses a disposable diaper having a skin facing surface and a non-skin facing surface on an opposite side thereof, and including a front waist region, a rear waist region, and a crotch region positioned between the front waist region and the rear waist region, and including a pair of leg openings, and a waist opening defined by side edges of the front and rear waist regions being connected. This diaper has a liquid absorbent structure disposed in the crotch region, and a stretchable sheet positioned on the skin facing surface in the front and rear waist regions, and intersecting to cover front and rear edges of the liquid absorbent structure, and a pocket (a three-dimensional guard) for collecting the body exudates is formed between the stretchable sheet and the front and rear edges of the liquid absorbent structure.

CITATION LIST

[Patent Literature 1] Japanese Patent Application Laid-open Publication No. 2001-252303

SUMMARY

Technical Problem

In the disposable diaper according to an invention disclosed in Patent Literature 1, by the pocket being formed in the front and rear waist regions, it is possible to collect and contain the body exudates flowed to the front and rear waist regions.

However, when the diaper is rolled up for disposal, the body exudates such as fecal exudates collected and contained in the pocket may leak from the waist opening.

An object of the present invention is to improve a conventional technology by providing a disposable wearing article capable of preventing the body exudates from leaking at the disposal.

Solution to Problem

The present invention is directed to a disposable wearing article having a vertical direction and a lateral direction, and a skin facing surface and a non-skin facing surface on an opposite side thereof, including a front waist region, a rear waist region, a crotch region positioned between the front waist region and the rear waist region, a pair of leg openings, and a waist opening defined by side edges of the front waist region and the rear waist region being coupled.

In the disposable wearing article according to the present invention, at least one of the front waist region and the rear waist region includes a pair of tape fasteners fixed to the non-skin facing surface of the side edges, and at least one of the front waist region and the rear waist region includes a pocket openable toward the crotch region, on the skin facing surface, and an upper end of a fixing part of the tape fastener is positioned at a lower side of a closing edge positioned on the waist opening side of the pocket in the vertical direction.

At least one of the front waist region and the rear waist region includes a belt-like area (belt area) positioned on the skin facing surface and extending in the lateral direction, and the pocket positioned on the non-skin facing surface, facing the belt-like area in the direction of thickness, at a middle part in the lateral direction, and the pocket includes a pocket outer area extending from the crotch region toward the waist opening, and a pocket inner area facing the pocket outer area and the belt-like area in the direction of thickness, and continuous with the pocket outer area, and connected to the belt-like area, and an upper end of the fixing part of the tape fastener is positioned at a lower side of an upper end of the pocket outer area in the vertical direction. Consequently, at disposal of the disposable wearing article after use, the pair of tape fasteners is connected at a lower side of the upper end of the pocket outer area in the vertical direction and a space of the pocket is maintained. Therefore, at disposal, it is possible to prevent the body exudates such as fecal exudates inside the pocket from leaking.

An upper end of the fixing part of the tape fastener is either positioned at a lower side of the pocket inner area in the vertical direction, or evens up a lower end. Consequently, when the tape fasteners in the pair are connected, it is possible to make large a space between the pocket inner area and the pocket outer area in the direction of thickness. Accordingly, it is possible to prevent assuredly the body exudates inside the pocket from leaking at disposal of the diaper.

The upper end of the fixing part of the tape fastener and the lower end of the pocket inner area even up in the vertical direction. Consequently, the pocket inner area and the pocket outer area are in even closer contact, and it is possible to prevent assuredly the body exudates inside the pocket from leaking.

The front waist area and the rear waist area have a first virtual line bisecting a dimension of the front waist region and the rear waist region in the vertical direction, and the tape fastener has a second virtual line bisecting a dimension of the tape fastener in the vertical direction, and the tape fastener is fixed to any one of the front waist region and the rear waist region such that the second virtual line is positioned at an upper side (is positioned above) the first virtual line. Consequently, at disposal of the disposable wearing article, when the crotch area is overlapped with one of the front waist region and the rear waist region, and thereafter, the tape fasteners are connected, since the tape fasteners can be connected on the waist opening side in the front and rear waist regions, it is possible to prevent the body exudates from leaking from the waist opening, and to roll up the disposable wearing article compactly.

The pocket is formed of two side parts of the pocket inner area and the pocket outer area, and further includes two pocket side areas folded inward in the lateral direction. Consequently, by having the two pocket side areas, it is possible to increase an amount of the body exudates that can be collected in the pocket.

The pair of tape fasteners has a base part formed of fibrous nonwoven fabrics, the fixing part positioned at one end of the base part and fixed to the non-skin facing surface of the rear waist region, and a free part positioned at the other end of the base part and extending outboard of the front waist region and the rear waist region in the lateral direction, and the free part has a fastening area that can be fastened to the base part. Consequently, at disposal of the disposable wearing article, since it is possible to fasten a fastening area of one tape fastener to the base part of the other tape fastener, and to bring both edges of the front and rear waist region closer when the pair of tape fasteners are connected to each other, and to make the pocket to be protruded toward the non-skin facing surface, it is possible to maintain the shape of the pocket, and to prevent the body exudates collected in the pocket from leaking.

Advantageous Effects of Invention

According to a disposable wearing article according to one or more embodiments of the present invention, the upper end of the fixing part of the tape fastener being positioned at the lower side of a closing edge positioned on the waist opening side of the pocket in the vertical direction, it is possible to maintain a space of the pocket. Accordingly, it is possible to prevent the body exudates such as fecal exudates inside the pocket from leaking.

BRIEF DESCRIPTION OF DRAWINGS

The drawings illustrate specific embodiments of the present invention including optional and preferred embodiments as well as essential features of the invention.

DESCRIPTION OF EMBODIMENTS

First Embodiment

A pull-on (pant-type) disposable diaper 10 shown as an example of a disposable diaper of the present invention has a vertical direction Y, a lateral direction X, a thickness direction Z (3-dimensional direction) intersecting each other, and an upward-downward direction (or the vertical direction Y) intersecting each other, and a vertical axis P extending along the vertical direction Y and bisecting a dimension thereof in the lateral direction X and a lateral axis Q extending along the lateral direction X and bisecting a dimension thereof in the vertical direction Y. In a worn state, a waist opening 21 is positioned at an upper side and leg openings 22 are positioned at a lower side. In the present description, 'overlapping each other in a planar view of the diaper 10' means overlapping each other in the thickness direction Z. Moreover, in the present description, 'pant-type disposable diaper' refers to all diapers irrespective of whether the diaper is with or without a leg hose or with a long or short hose, at part of inserting both legs.

Figure 1:
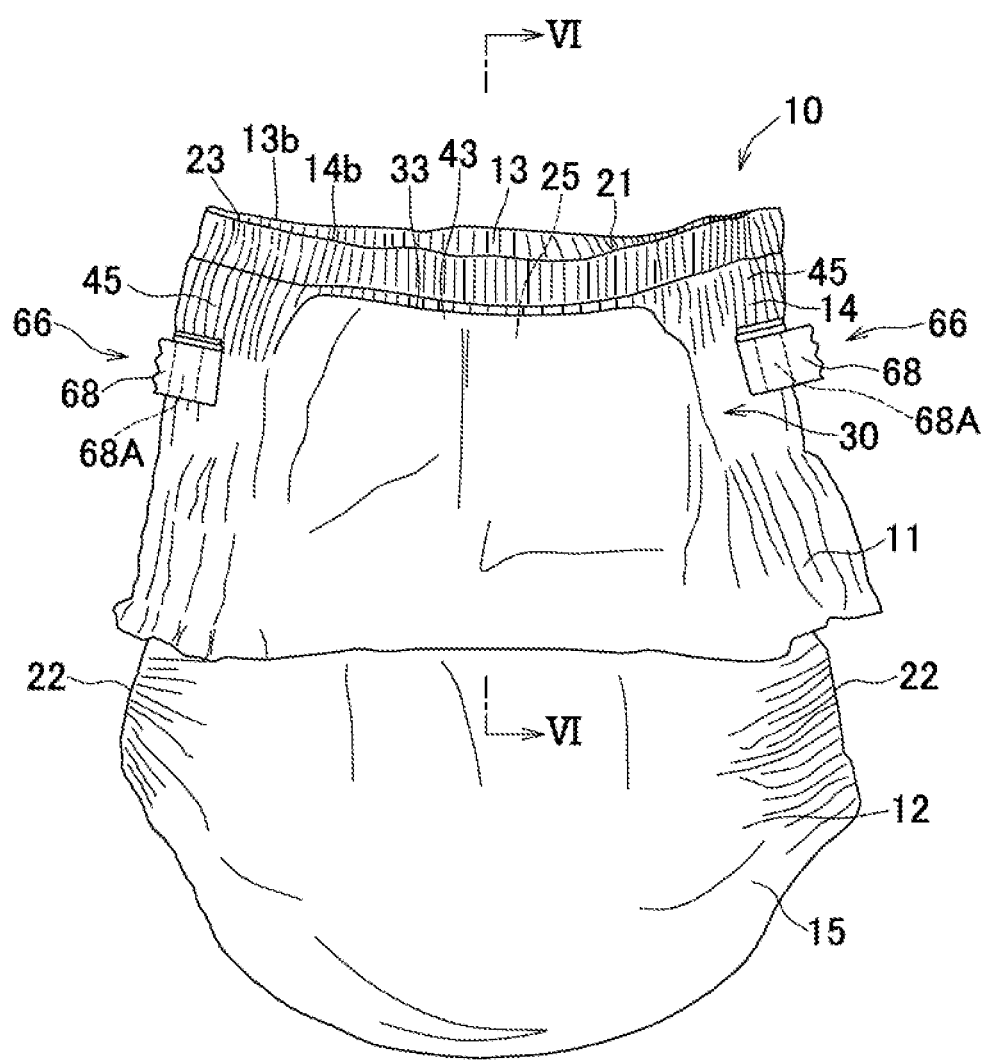
FIG. 1 is a rear view of a disposable wearing article (diaper) according to a first embodiment of the present invention.
Figure 2:
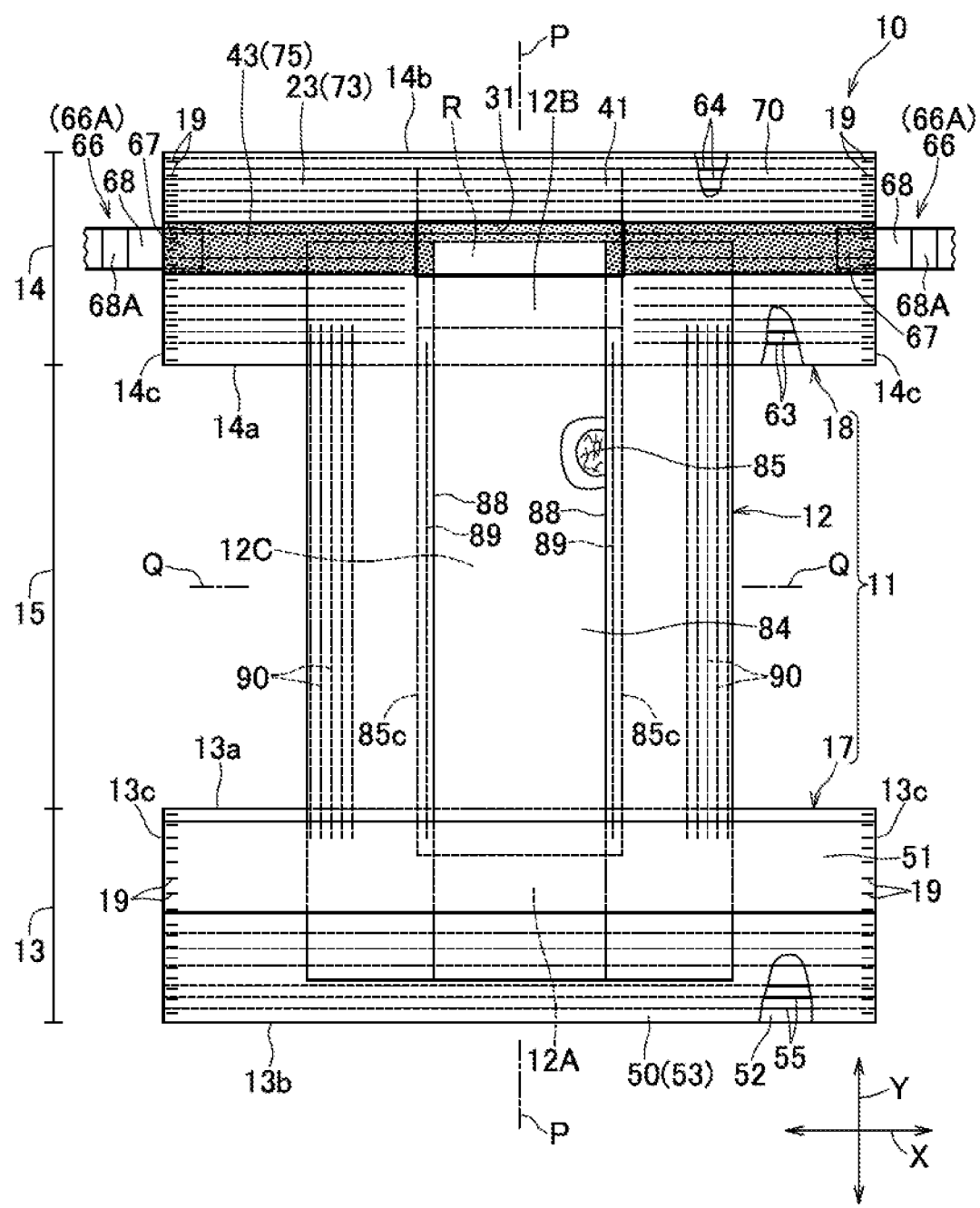
FIG. 2 is a partially cutaway planar view showing an unfolded state of a diaper in a state of elastic members elongated in a vertical direction and a lateral direction.

Referring to FIG. 1 and FIG. 2, the diaper 10 includes a skin facing surface and a non-skin facing surface opposite to the skin facing surface, an elastic waist panel 11 having an annular shape extending in a direction around the waist, an absorbent chassis 12 joined to the elastic waist panel 11, a front waist region 13, a rear waist region 14, and a crotch region 15 positioned between the front and rear waist regions 13, 14. The diaper 10 is formed symmetrically about the vertical axis P, and the elastic waist panel 11 includes a front waist panel 17 positioned on the front waist region 13, and a rear waist panel 18 positioned on the rear waist region 14.

The front and rear waist regions 13, 14 have an oblong rectangular shape defined by inner end edges 13a, 14a extending in the lateral direction X, outer end edges (front and rear waist opening edges) 13b, 14b extending in the lateral direction X, and side edges 13c, 14c extending in the vertical direction Y respectively. Both side edges 13c of the front waist region 13 and both side edges 14c of the rear end regions 14 respectively overlap with each other, and are coupled along side seams 19 continually in the vertical direction Y, thereby forming two side edges, the waist opening 21, and a pair of leg openings 22. The side seams 19 are made by a well-known joining means such as various known thermal welding means, for example, heat embossing/debossing, and ultrasonic processing.

<Pocket>

Figure 6:
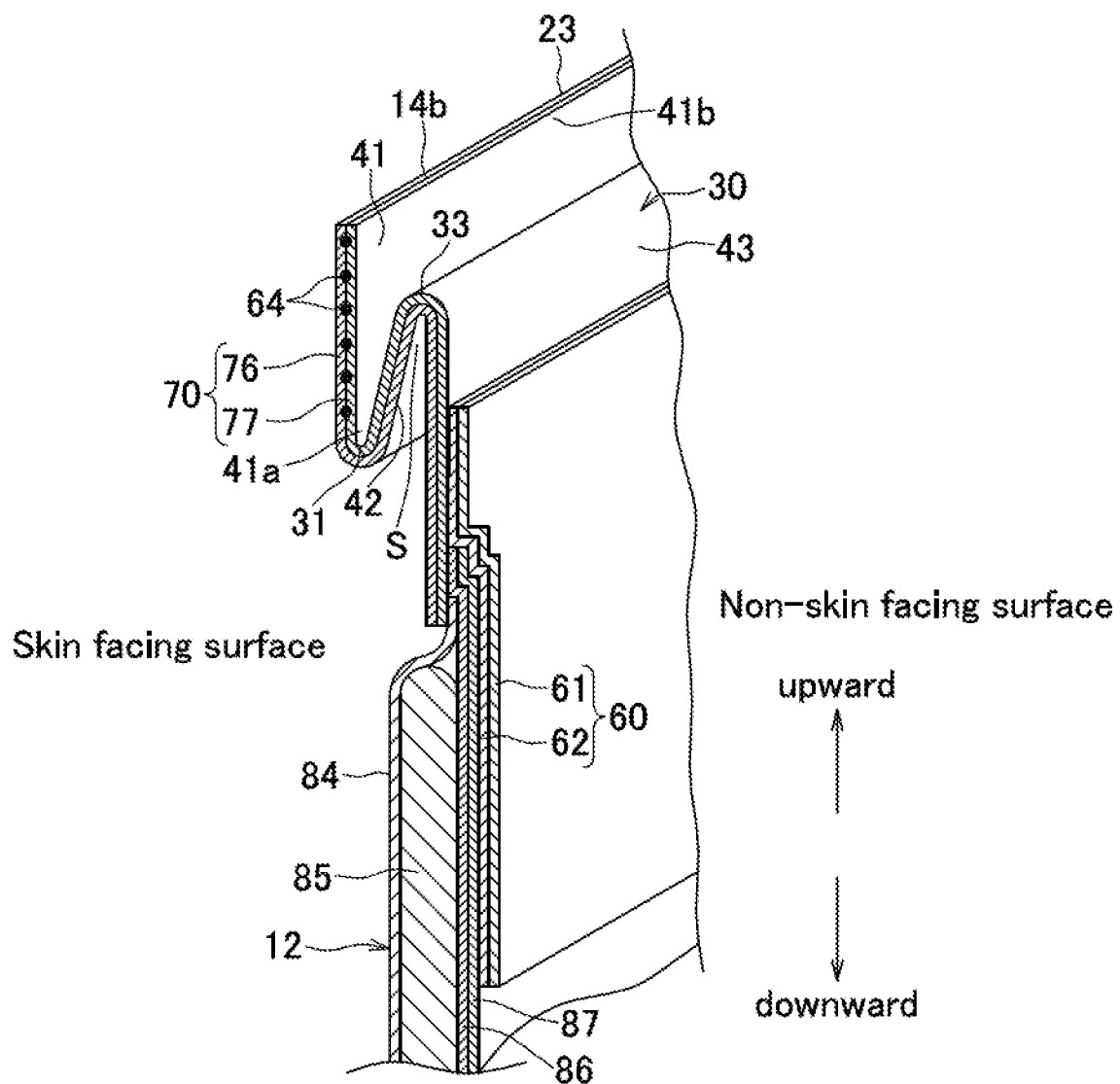
FIG. 6 is a schematic cross-sectional view along line VI-VI shown in FIG. 1.

Referring to FIG. 1 and FIG. 6, the diaper 10 includes a belt-like (hereinafter, 'belt area') 23 put in contact with the body of the wearer (an area put in contact with skin of the wearer positioned on the skin facing surface) adjacent to the waist opening 21 of the rear waist region 14, a middle part 41 positioned at the almost middle of the rear waist region 14 in the lateral direction X, in the belt area 23 having an outer end part (site) 41b and an inner end part (site) 41a. The diaper 10 includes a pocket 30 adjacent to the belt area 23, in a frontward-rearward direction in the worn state. The pocket 30 is formed over a predetermined area in the lateral direction X, with the vertical axis P as a center and is openable downward (toward the crotch region). The belt area 23 and an opening edge (folding part 31) of the pocket 30 are positioned on the waist opening 21 side of the rear waist region 14. Here, 'waist opening 21 side of the rear waist region 14' refers to an area on the outer end edge 14b side of a first virtual line L1 (FIG. 4) bisecting a dimension of the rear waist region 14 in the vertical direction Y.

The pocket 30 is defined by a pocket outer area 43 facing the middle part 41 of the belt area 23 in the frontward-rearward direction, and extending upward from the crotch region 15 side, and a pocket inner area 42 facing the pocket outer area 43 and the belt area 23 respectively in the frontward-rearward direction, and continuous with the pocket outer area 43 via a folding part 33 extending in the lateral direction X, and connected to the inner end part 41a of the middle part 41 of the belt area 23 extending downward from the folding part 33. By the pocket inner area 42 and the middle part 41 of the belt area 23 being connected, the folding part 31 folded in the downward direction is defined. Both side parts of the pocket inner and outer areas 42, 43 overlap with each other and fixed, two side areas 45 of the pocket inner and outer areas 42, 43 that have been fixed, are fixed to two side parts of the belt area 23. The two side areas 45 being extended inward in the lateral direction X from the side seams 19, the pocket 30, at least, has a size of the extent of opening at a middle part of the rear waist region 14, and not a size of opening between the side seams 19. The pocket 30 includes the folding part 31 folded in the downward direction and a folding part 33 folded toward the waist opening 21 (upward direction). In the present embodiment, the folding part 33 is a closing edge of the pocket 30 positioned on the waist opening 21 side, while the folding part 31 is an opening edge of the pocket 30.

<Elastic Waist Panel>

Figure 5:
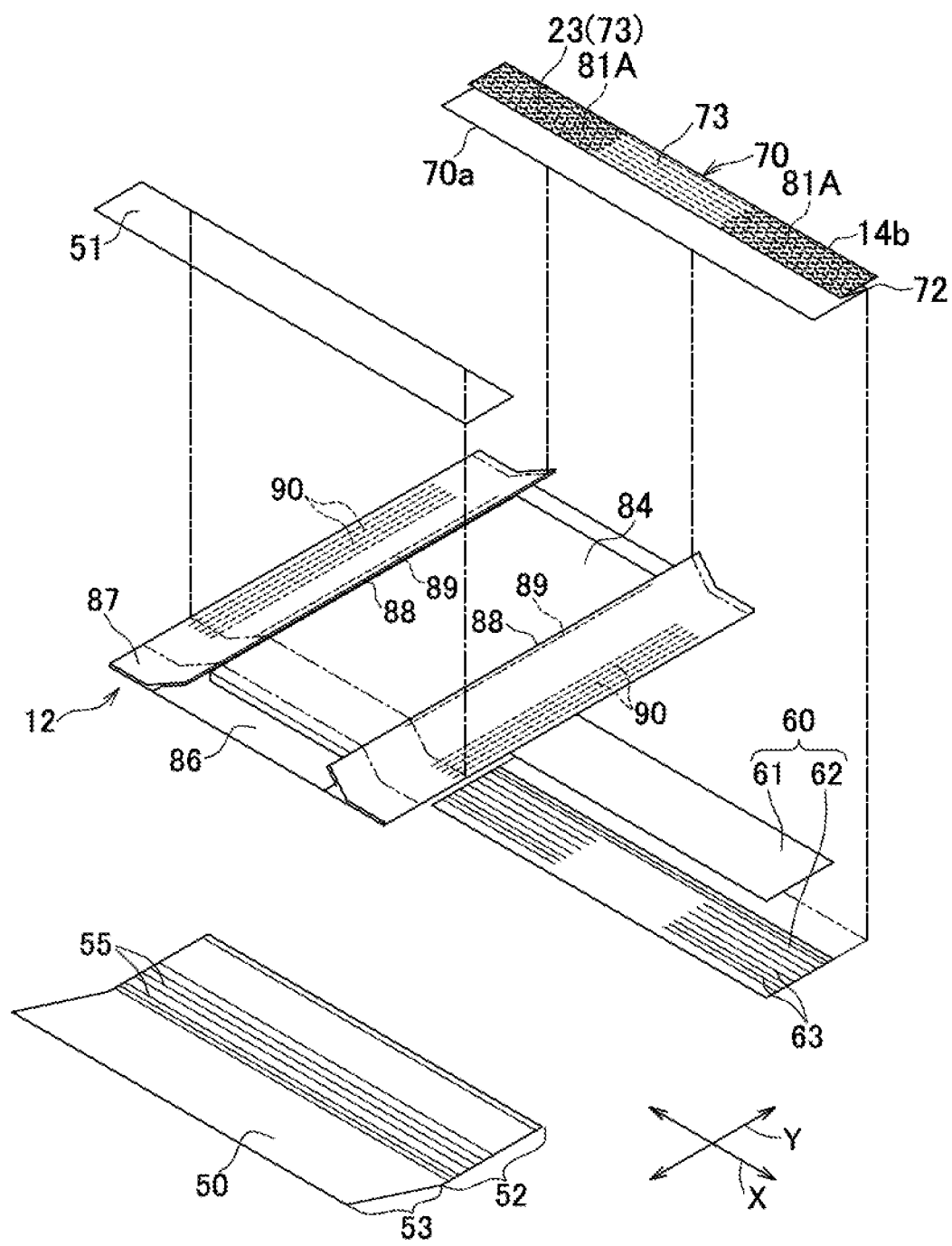
FIG. 5 is a partially cutaway exploded perspective view of the diaper.

Referring to FIG. 2 and FIG. 5, the front waist panel 17 includes a front waist sheet 50 defining an outer counter of the front waist region 13. The front waist sheet 50 includes a main part 52 in which a front end part 12A of the absorbent chassis 12 is disposed, and an extending part 53 positioned outboard of the main part 52 in the vertical direction Y. The extending part 53 is fixed to the main part 52 folded inward in the vertical direction Y along a folding line extending in the lateral direction X, and the front end part 12A of the absorbent chassis 12 disposed on an inner surface of the main part 52. Between the extending part 53 and the main part 52 of the front waist sheet 50, a plurality of string- or strand-like front waist elastic members extending in the lateral direction X is secured contractively in an elongated state.

A front elastic sheet 51 stretchable in the lateral direction X is disposed in the front waist sheet 50, on the crotch region 15 side of the front waist elastic member 55. The front elastic sheet 51 is positioned on the skin facing surface, covering the front end part 12A of the absorbent chassis 12, and is fixed to the main part 52 positioned on both sides thereof.

The rear waist panel 18 includes a rear waist sheet 60 including an inner surface sheet 61 positioned on the skin facing surface and an outer surface sheet 62 positioned on the non-skin facing surface, and a plurality of string- or strand-like lower rear waist elastic members 63 extending in the lateral direction X, secured contractively in an elongated state between the inner and outer surface sheets 61, 62. A base sheet 70 in the form of being folded back in a substantially cross-section Q shape is disposed in the rear waist region 14, at an outer end part of the rear waist panel 18.

<Base Sheet>

Figure 3A:
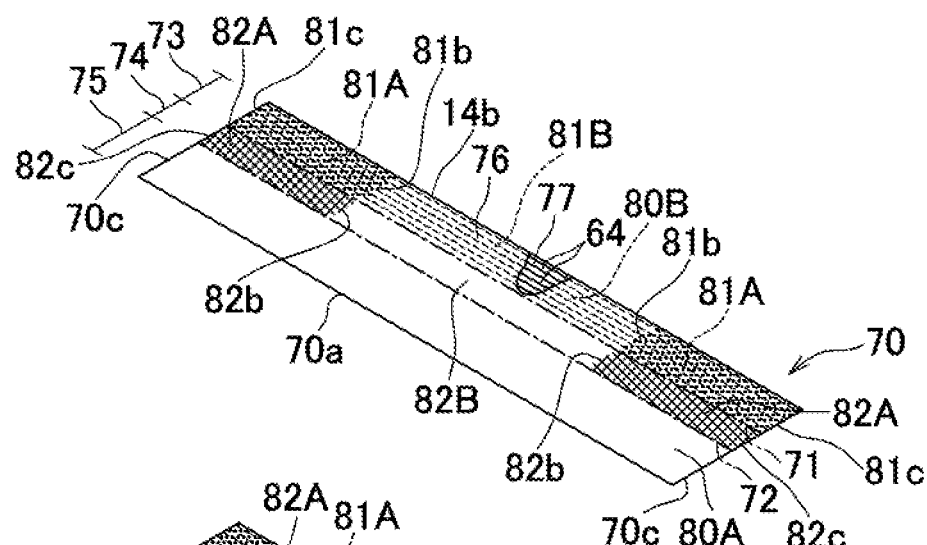
FIG. 3A is a partially cutaway planar view of an unfolded base sheet.

Referring to FIG. 3A, the base sheet 70 has an inner end edge 70a and an outer end edge (rear waist opening edge) 14b extending in the lateral direction X, a first surface 80A (skin facing surface) having an oblong rectangular shape defined by side edges 70c extending in the vertical direction Y between the inner and outer end edges 14b and 70a, and a second surface 80B (non-skin facing surface) positioned on opposite side of the first surface 80A, and a first folding line 71 and a second folding line 72 extending parallel to the lateral direction X. The base sheet 70 has an outer end part 73 positioned between the outer end edge 14b and the first folding line 71, an intermediate part 74 positioned between the first folding line 71 and the second folding line 72, and an inner end part 75 positioned between the second folding line 72 and the inner end edge 70a. A pair of first fixing areas 81A positioned to be opposite in the lateral direction X is disposed on the second surface 80B side of the outer end part 73, and a first non-fixing area 81B extending in the lateral direction X is positioned between the first fixing areas 81A. A pair of second fixing areas 82A positioned to be opposite in the lateral direction X is disposed on the first surface 80A of the intermediate part 74, and a second non-fixing area 82B extending in the lateral direction X is positioned between the second fixing areas 82A. The first fixing areas 81A are for fixing the belt area 23 and the pocket inner area 42, and the second fixing areas 82A are for fixing the pocket inner area 42 and the pocket outer area 43. In the first non-fixing area 81B, the belt area 23 and the pocket inner area 42 are not fixed, and in the second non-fixing area 82B, the pocket inner area 42 and the pocket outer area 43 are not fixed.

Figure 3B:
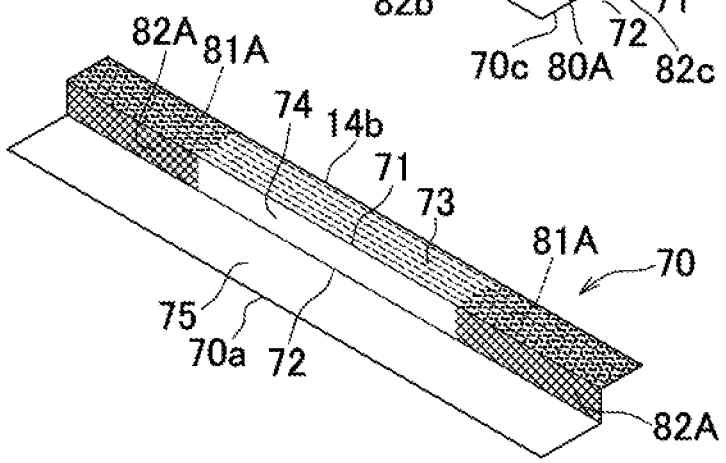
FIG. 3B is a diagram showing as to how to fold the base sheet.
Figure 3C:
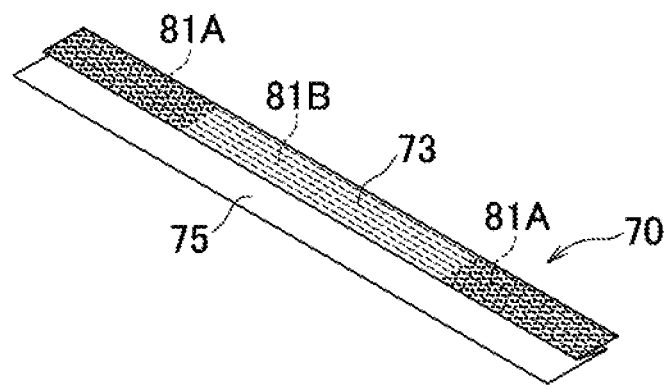
FIG. 3C is a diagram showing a state in which the base sheet is folded along a first and second folding lines.

The base sheet 70 further has an inner surface sheet 76 positioned on the skin facing surface, an outer surface sheet 77 positioned on the non-skin facing surface, and a plurality of string- or strand-like upper rear waist elastic members 64 secured contractively in an elongated state between the inner and outer surface sheets 76, 77, extending in the lateral direction X in the outer end part 73. Referring to FIGS. 3B and 3C, the base sheet 70, by being folded along the first folding line 71 such that the second surface 80B side of the outer end part 73 and the second surface 80B side of the intermediate part 74 come in contact with each other, and by being folded along the second folding line 72 such that the first surface 80A side of the intermediate part 74 and the first surface 80a side of the inner end part 75 come in contact with each other, a state of being folded in a substantial Z-shape in a vertical cross section is maintained.

The first fixing areas 81A and the second fixing areas 82a are extending continuously in the lateral direction X, and dimensions thereof in the lateral direction X are almost equal, and dimensions in the lateral direction X of the first and second non-fixing areas 81B, 82B positioned between the first fixing areas 81A and the second fixing areas 82A are almost equal. The first and second fixing areas 81A, 82A have internal parts 81b, 82b positioned at an inner side (positioned inside) virtual lines L3 that are extension of two side edges 85c of an absorbent body 85, and external parts 81c, 82c positioned at an outer side of the virtual lines L3. The external parts 81c, 82c overlap with the side seams 19. Moreover, the first and second non-fixing areas 81B, 82B are positioned to overlap with each other in a planar view of the diaper 10. The first and second fixing areas 81A, 82A are formed by applying a well-known adhesive such as hot-melt adhesives, or a well-known heat welding means such as heat-sealing.

Referring to FIG. 2, the base sheet 72 is fixed to the absorbent chassis 12 and the rear waist panel 18 via a fixing area (third fixing area) 83 having a concave shape toward the lateral axis Q. The third fixing area 83 is positioned to be opposite in the lateral direction X and has the same shape and size as of the first and second fixing areas 81A, 82A, and includes a base part 83a overlapping with the first and second fixing areas 81A, 82A in a planar view of the diaper 10, and a connecting part 83b connecting the pair of base parts 83a and not overlapping with the first and second fixing areas 81A, 82A in the planar view of the diaper 10. The base sheet 70 being fixed in a state of being folded by the plurality of folding lines, the belt area 23 of the rear waist area 14 is formed by the outer end part 73, the pocket inner area 42 is formed by the second non-fixing area 82B of the intermediate part 74, and the pocket outer area 43 is formed by a portion of the inner end part 74 facing the second non-fixing area 82B. Moreover, both side parts of the pocket inner area 42 and both side parts of the pocket outer area 43 are joined in a state of being overlapped via the second fixing area 82A.

In the present embodiment, the pocket 30 is formed by fixing the base sheet 70 which is separate from the rear waist sheet 60. However, for exerting a technical effect of the present invention, the rear waist sheet 60 and the base sheet 70 may be formed of a single sheet, and the belt area 23 may be formed of a sheet member same as the rear waist sheet 60, and the pocket 30 may be formed by fixing a separate sheet member to the belt area 23. Moreover, the base sheet 70 may be formed of one elastically stretchable fibrous nonwoven fabric sheet, or instead of an upper rear waist elastic member 64, an elastically stretchable fibrous nonwoven fabric sheet may be disposed between the inner and outer surface sheets 76, 77. Consequently, in the present description, an expression 'the pocket inner area 42 is connected to the inner end part 41a of the middle part 41 of the belt area 23' includes the case where the middle part 41 and the pocket inner area 42 are formed of the same sheet member, and are folded at the folding part 31, and the case where the middle part 41 and the pocket inner area 42 are formed of separate sheet members, and the two sheet members are connected at the folding part 31. Moreover, the pocket 30 can also be formed by extending rearward the sheet member forming the absorbent chassis 12, and folding the rear waist panel and a portion extending further rearward of the rear waist panel.

Figure 4:
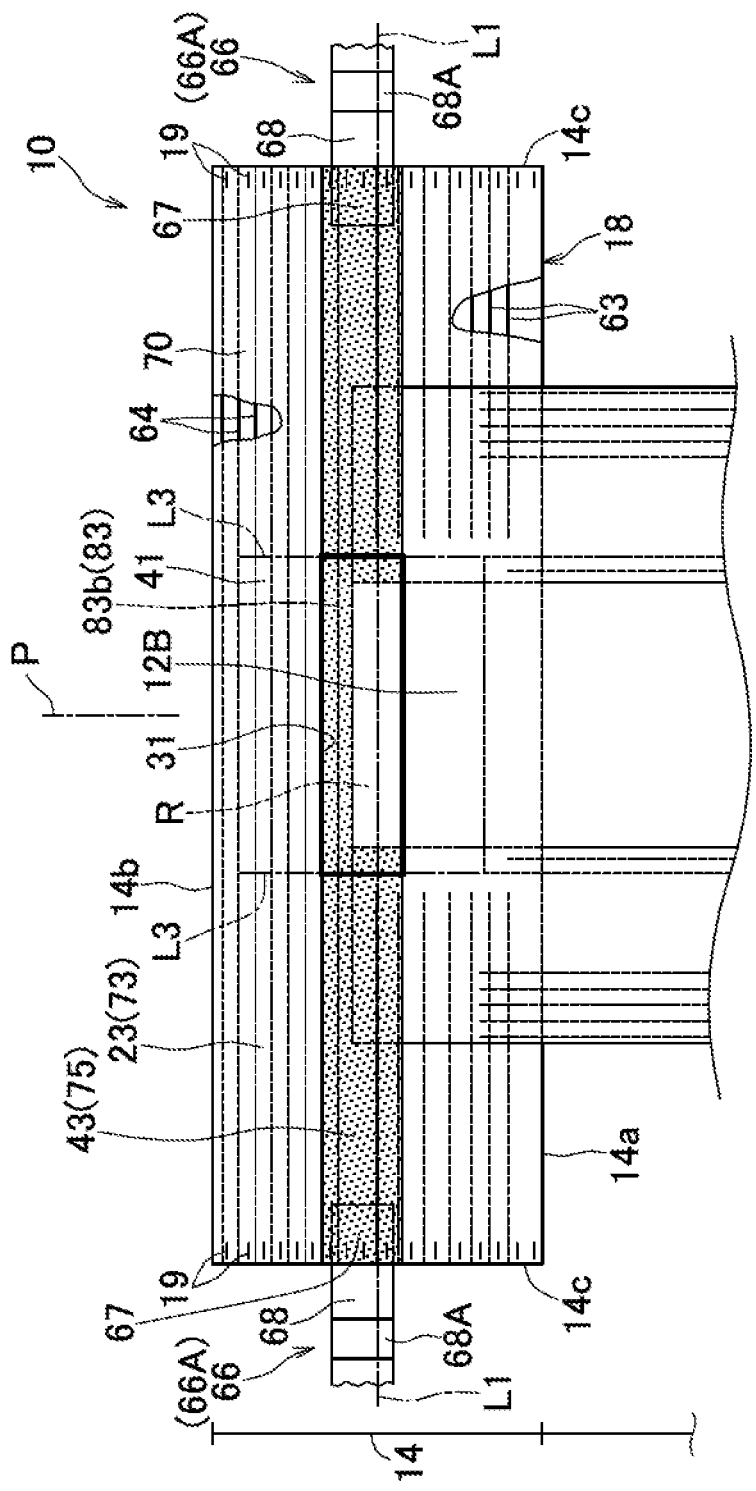
FIG. 4 is a partially enlarged view of a rear waist region.
Figure 7:
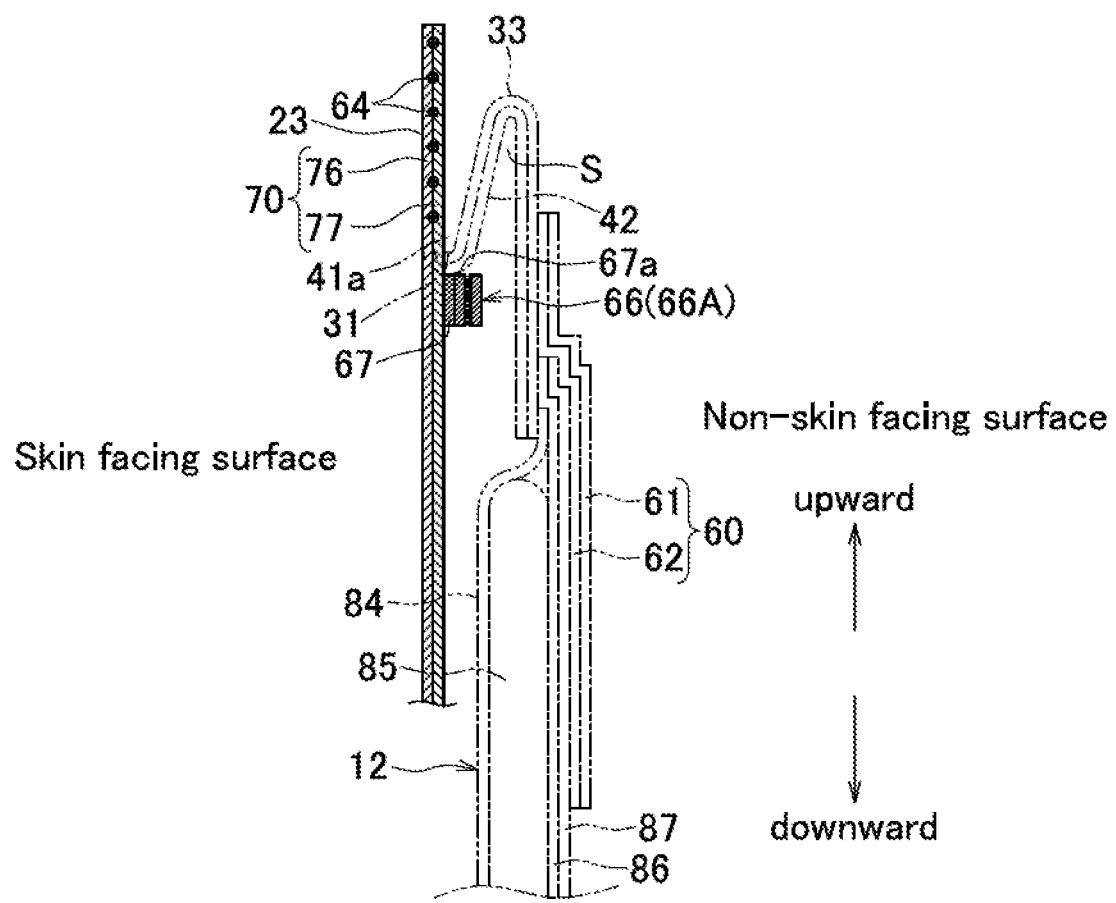
FIG. 7 is a cross-sectional view of the diaper in an unfolded state upon cutting away the two side areas of the front and rear waist regions.

Referring to FIG. 1, FIG. 2, and FIG. 7, a pair of tape fasteners 66 is disposed on two side parts of the rear waist region 14 positioned outboard of the pocket 30 in the lateral direction X. In FIG. 1, a state of the tape fasteners 66 folded in Z-shape and reverse Z-shape is shown, and in FIG. 2, an unfolded state of the tape fasteners 66 folded, is shown. The tape fastener 66 includes a fixing part 67 fixed to the side edge 14c, and a free part 68 extending outward from the fixing part 67 in the lateral direction X, and in the unfolded state, has a long rectangular shape in the lateral direction X as shown in FIG. 4. Before and during the use of the diaper 10, the tape fasteners 66 maintain a folded state by temporary fixing parts, whereas, at disposal of the diaper 10, the joining by the temporary fixing part is unfastened to unfold.

The fixing part 67 and the free part 68 of the tape fastener 66 include a base part 66A formed of fibrous nonwoven fabrics, and a fastening area 68A disposed on the free part 68 in the base part 66A. The fastening area 68A can be formed by a set of hooks of a mechanical fastener or a pressure-sensitive adhesive, and can be fastened to the base part 66A formed of fibrous nonwoven fabrics. In other words, the base part 66A functions as a loop set of the mechanical fasteners for the fastening area 68A. After the fastening area 68A and the base part 66A are joined, the joint of the fastening area 68A and the base part 66A can be released by applying a pressure to both of the fastening area 68A and the base part 66A. Moreover, the fastening area 68A can be fastened to and peeled-off from a non-skin facing surface of the front waist region 13 and a non-skin facing surface of the crotch region 15.

FIG. 7 is a cross-sectional view of the diaper 10 in the unfolded state upon cutting away the two side edges 13C, 14C of the front and rear waist regions 13, 14. An upper end 67a of the fixing part 67 of the tape fastener 66 is positioned at a lower side of the folding part 33 which is a closing edge positioned on the waist opening 21 side of the pocket 30 in the vertical direction Y. More specifically, in the present embodiment, the upper end 67a of the fixing part 67 of the tape fastener 66 and the folding part 31 which is a lower end of the pocket inner area 42 even up in the vertical direction Y.

<Absorbent Chassis>

Referring to FIG. 2 and FIG. 5, the absorbent chassis 12 has a rectangular shape, and includes the front end part 12A, a rear end part 12B, and an intermediate part 12C positioned between the front and rear end parts 12A, 12B. The absorbent chassis 12 includes a body side liner 84 made of liquid permeable fibrous nonwoven fabrics positioned on the skin facing surface, an absorbent body 85 which is liquid absorbent, a leakage barrier sheet 86 formed of a liquid impermeable plastic film covering an entire bottom surface of the absorbent body 85, and a covering sheet 87 which is either liquid impermeable or liquid hardly-permeable forming an entire non-skin facing surface of the absorbent chassis 12. The absorbent body 85 includes a core material formed from a mixture of materials such as fluff pulp and absorbent polymer particles, and a liquid-absorbent and diffusive core wrapping sheet such as a tissue paper with which the entire core is wrapped.

The covering sheet 87 has side parts outboard of side edges of the leakage barrier sheet 86 in the lateral direction X. The side parts are folded inward (toward the absorbent body 85) along folding lines extending in the vertical direction Y, adjacent to both side edges of the leakage barrier sheet 86, and fixed to the body side liner 84. The side portions have both edge fixing parts fixed to the body side liner 84 and spaced apart from each other in the vertical direction Y, proximal edges fixed to side edges of the body side liner 84, and distal edges (free edges) 88 extending in the vertical direction Y between both edge fixing parts, and extending parallel to the distal edges 88 in the vertical direction Y. The distal edges 88 each have a sleeve shape formed by folding and fixing outer edges of the covering sheet 87, and a plurality of string- or strand-like cuff elastic members 89 extending in the vertical direction Y secured contractably in an elongated state. By the cuff elastic members 89 being contracted, the edges are spaced apart toward the body of the wearer from the body side liner 84 and form a barrier cuff, and fit the thighs of the wearer thereby preventing the leakage of body exudates. Moreover, a plurality of string- or strand-like leg elastic members 90 extended in the vertical direction Y is fixed contractively in an elongated state to both side parts of the covering sheet 87.

The leg elastic members 90 being composed of a plurality of elastic materials disposed at a predetermined spaced-apart dimension in the lateral direction X and form an elastic belt which is flexible, at a constant width, may fit in the sheet form around legs of the wearer in the worn state, and prevent effectively the lateral leakage of the body exudates. Moreover, a rear end part of the leg elastic members 90 overlaps in a planar view with the lower rear waist elastic members 63 in the rear waist region 14. By the leg elastic member area on which a contractile force of the leg elastic members 90 acts, and the waist elastic member area on which a contractile force of the lower rear waist elastic members 63 overlapping in a planar view acts, a virtual elastic belt (band) surrounding the thighs of the wearer is formed.

Referring to FIG. 2 and FIG. 6, the base sheet 70 is fixed to the belt area 23 and the rear end part 12B of the absorbent chassis 12 via the fixing area 83, and is not fixed to the rear end part 12B of the absorbent chassis 12 at a portion between the distal edges 88 of the covering sheet 87. By the base sheet 70 having such joining mode, a rear space R for collecting and containing body exudates flowed to the rear waist region 14 is defined between the non-fixing area and the rear end part 12B of the absorbent chassis 12.

Since a few-month-old baby usually excretes (passes) loose stool in a fluid form in various postural situations such as being held in hands of mother at the time of breast feeding, the loose stool may leak from the rear waist region 14 at the waist opening 21 or the loose stool may get stuck to a dorsal side of the wearer, thereby making it dirty. Moreover, while the diaper 10 is worn, in the front waist region 13, a space that can accommodate (collect) the body exudates when the waist opening part slips down may be formed between the body and the diaper 10, and in the rear waist region 14, a gap (space) is not susceptible to be formed as the buttocks has a protruded outer counter, for collecting and containing the body exudates temporarily, as the diaper 10 according to the present embodiment, in the worn state, the pocket 30 having a pocket space S is formed by the belt area 23, the pocket inner area 42, and the pocket outer area 43.

In the present embodiment, since the belt area 23 and the pocket 30 are positioned on the waist opening side of the rear waist region 14, and the belt area 23 fits the wearer's body by a tensile stress of the upper rear waist elastic member 64, the body exudates flowed from the crotch region 15 side toward the rear waist opening side is prevented from leaking and the body exudates having the movement thereof inhibited, inflows into the pocket space S extending upward in a convex shape, and collected and contained temporarily. In such manner, by letting the body exudates having the movement thereof inhibited to enter into the pocket 30 positioned on the rear surface of the rear waist region 14, it is possible to suppress a feeling of discomfort or a skin trouble due to the body exudates coming in contact with the body. Since the pocket 30 is not elongated and contracted in conjunction with the belt area 23, even when the rear waist region 14 is elongated, the pocket opening may not close. Moreover, the pocket 30 being positioned at the upper side of the upper end part (rear end part) of the absorbent body 85, is capable of collecting the body fluid flowed toward the rear waist opening without being absorbed in the absorbent body 85.

Moreover, a portion of the base sheet 70 forming the pocket 30 is joined to the rear waist region 14 via the fixing area 83 extending inward in the lateral direction X from the side seams 19, and the base sheet 70 is positioned outboard of the leg elastic members 90 and the cuff elastic members 89 in the vertical direction Y, and overlap with the leg elastic members 90 and the cuff elastic members 89 in a planar view of the diaper 10. Therefore, even when a contractile force of the leg elastic members 90 and the cuff elastic members 89 is exerted indirectly to the pocket outer area 43 and the force is exerted to pull the pocket outer area 30 downward, the pocket space S may not disappear due to the folding part 33 falling apart by the pocket outer area 43 being pulled downward.

Referring to FIG. 6, in the diaper 10, when the body exudates such as fecal exudates is excreted in the pocket 30, since the folding part 33 which is an opening edge of the pocket 30 is folded upward of the non-skin facing surface side, it is possible to collect a large amount of body exudates in the pocket 30.

Figure 8:
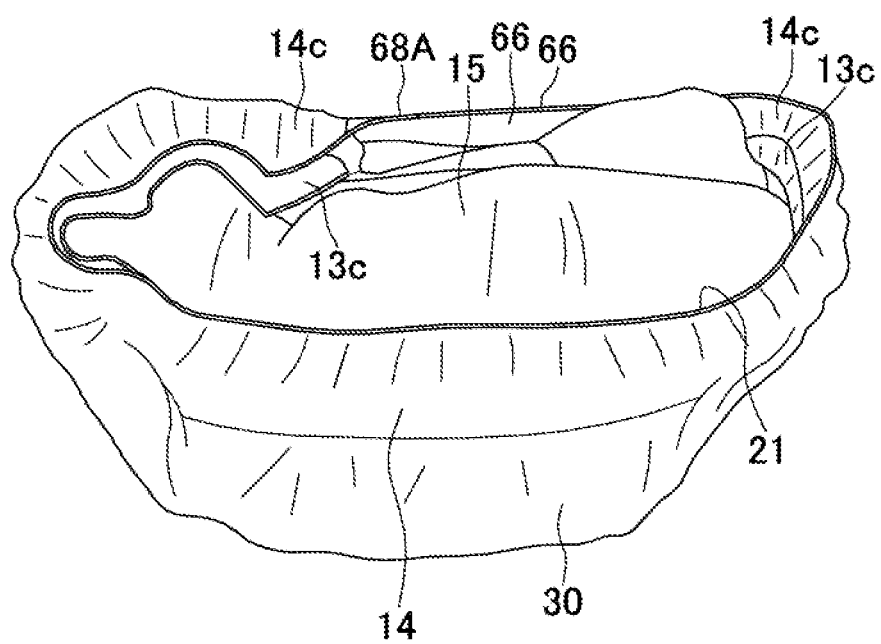
FIG. 8 is a planar view when a state of the pair tape fasteners connected at disposal of is viewed from the waist opening side.

FIG. 8 is a planar view when a state of the diaper 10 when rolled-up for disposing of is viewed from the waist opening 21 side. For disposal of the diaper 10, first, both end edges 13c of the front waist region 13 are tore off, and the diaper 10 is taken off the wearer's body. Next, the front waist region 13 and the rear waist region 14 are made to be opposed to each other to come in contact with each other, and the diaper 10 is folded such that the front waist region 13 and the crotch region 15 are opposed to each other. Thereafter, the tape fasteners 66 in the folded state are unfolded, and the fastening area 68A of one of the tape fasteners 66 is fastened to the base part 66A of the other tape fastener 66, and the two tape fasteners 66 are connected to each other. As the two tape fasteners 66 are connected, both side edges 13c, 14c of the front and rear waist regions 13, 14 come closer, and also it is possible to let the pocket 30 to be protruded toward the non-skin facing surface of the rear waist region 14. Accordingly, it is possible to maintain the shape of the pocket 30, and to prevent the body exudates such as fecal exudates accommodated (collected) in the pocket 30 from leaking.

According to the diaper 10 according to the present embodiment, the upper end 67a of the fixing part 67 of the tape fastener 66 being positioned at the lower side of the folding part (closing edge) 33 positioned on the waist opening 21 side of the pocket 30 in the vertical direction Y (see FIG. 7), even when the two tape fasteners 66 are connected, it is possible to maintain the space of the pocket 30. Accordingly, at disposal of the diaper 10, it is possible to prevent the body exudates inside the pocket 30 from leaking. To describe in further detail, even when the tape fasteners 66 are elongated and connected to each other, the force connecting the tape fasteners 66 is not susceptible to act on the folding part 33 which is a closing edge, and the pocket 30 not being compressed in the thickness direction Z, it is possible to maintain an internal space of the pocket 30.

Moreover, since the upper end 67a of the fixing part 67 of the tape fastener 66 and the folding part 31 which is the lower end of the pocket inner area 42 even up in the vertical direction Y (see FIG. 7), when the two tape fasteners 66 are connected, it is possible make large a space between the pocket outer area 43 and the pocket inner area 42 in the direction of thickness. Accordingly, at disposal of the diaper 10, it is possible to prevent assuredly the body exudates inside the pocket 30 from leaking. To describe in further detail, by the upper end 67a of the fixing part 67 of the tape fastener 66 and the folding part 31 which is the lower end of the pocket inner area 42 evening up, since the force connecting the two tape fasteners 66 acts to close the opening edge (folding part 31) of the pocket 30, a gap is not susceptible to open at the opening edge (folding part 31) after both side edges 13c, 14c of one of the front and rear waist regions 13, 14 are cut away, thereby enabling to prevent assuredly the body exudates from leaking.

Second Embodiment

Figure 9:
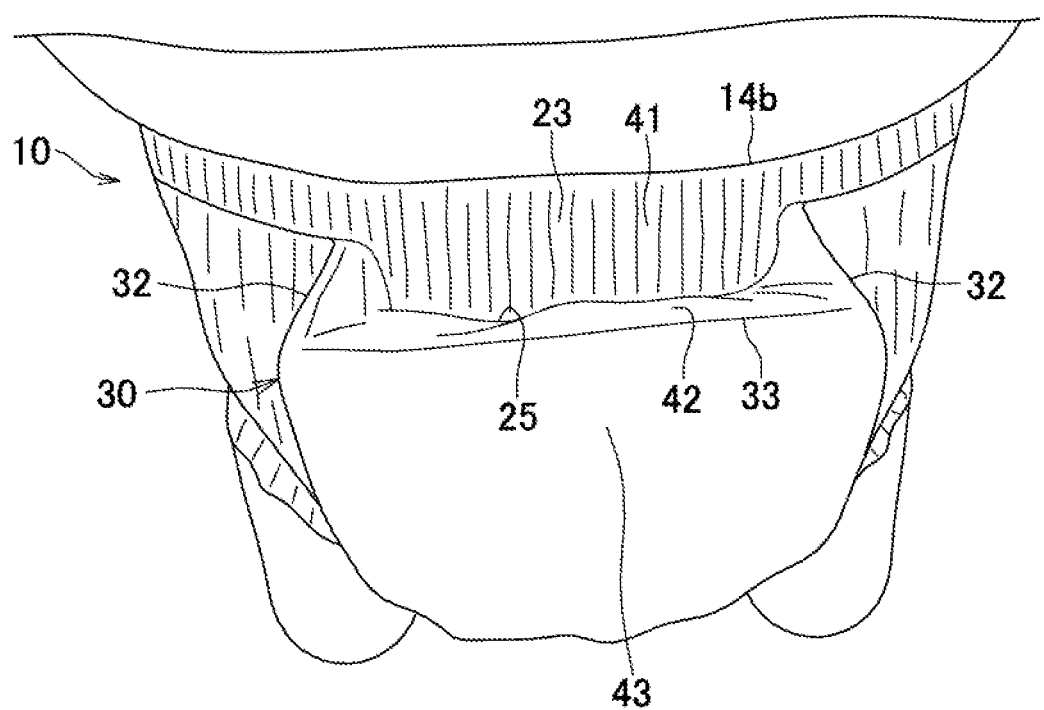
FIG. 9 is a perspective view showing a diaper of a second embodiment in a worn state.

A worn state of the diaper 10 of a second embodiment is shown in FIG. 9. The pocket 30 of the diaper 10 is defined by the pocket inner and outer areas 42, 43, and pocket side areas 32 including both side parts of the pocket inner and outer areas 42, 43, and tucked inward in the lateral direction X. Both side parts of the pocket inner and outer areas 42, 43 are overlapped with each other and form the pocket side areas 32, and both side areas 45 made of a portion other than the pocket side areas 32 are fixed to both side parts of the belt area 23.

The pocket side area 32 is tucked inward (toward the vertical axis P) of the lateral direction X. In a state of the folding parts 31, 33 and the pocket side areas 32 unfolded in the worn state of the diaper 10, a concave part 25 opening upward is formed between the middle part 41 and the pocket 30. The pocket side areas 32, in so long as are tucked stretchably, a plurality of folding lines extending in the vertical direction may be formed by being folded in plurality including portions folded unintentionally.

The pocket 30 has the folding part 31 folded in the downward direction, pocket side areas 32 tucked inward of the lateral direction X, and the folding part 33 folded toward the waist opening 21 (upward direction), and by the folding part 31, the pocket side areas 32, and the folding part 33 being folded in directions different from each other (three directions), the pocket side areas 32 rises when the belt area 23 is extended in the direction around the waist, and the pocket inner area 42 moves rearward to be separated away from the middle part 41 of the belt area 23.

Figure 10:
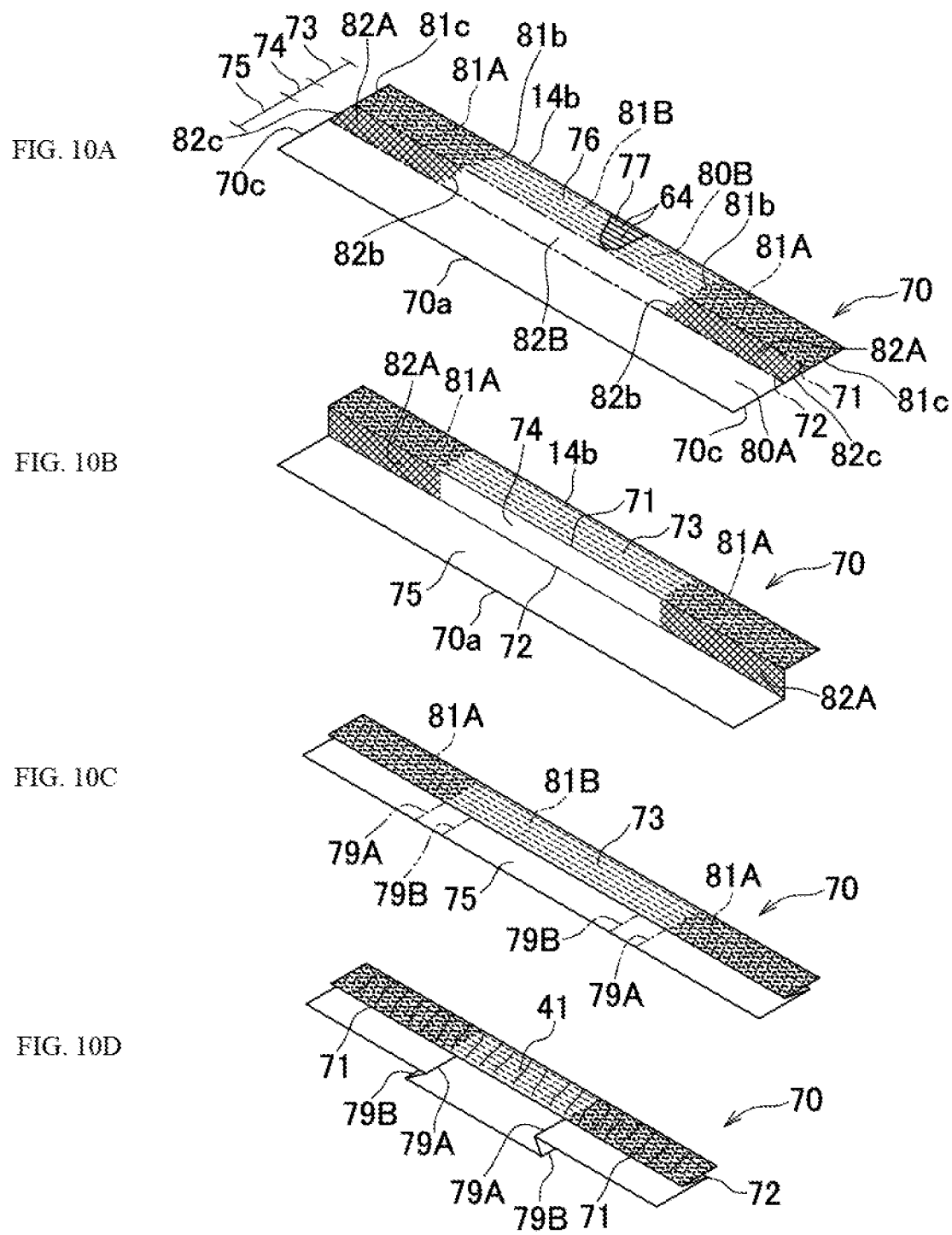
FIG. 10A is a partially cutaway planar view of an unfolded base sheet.
FIG. 10B is a diagram showing as to how to fold the base sheet.
FIG. 10C is a diagram showing a state in which the base sheet is folded along a first and second folding lines.
FIG. 10D is a diagram showing a state in which the base sheet is folded along a third folding line.

The base sheet 70 of the diaper 10 is shown in FIG. 10. FIGS. 10A, 10B being the same as FIGS. 3A, 3B, description thereof is omitted.

In states shown in FIGS. 10A to 10C, a force in a direction away from each other in the lateral direction X is applied to both side parts of the base sheet 70. However, referring to FIG. 10D, in the base sheet 70, the outer end part 73 is contracted due to the upper rear waist elastic members 64, and from a state of the base sheet 70 being folded along the first and second folding lines 71, 72, and joined via the first and second fixing areas 81A, 82A, by further folding the intermediate part 74 and the inner end part 75 that are stacked, along a pair of third folding lines 79A and a pair of fourth folding lines 79B (mountain-fold folding lines) extending in the vertical direction Y along the side edges of the second non-fixing area 82B, a portion of the base sheet 30 excluding the outer end part 73 (intermediate part 74 and the inner end part 75) has a cross-section Q shape. A dimension in the lateral direction X of the base sheet 70 in such folded state is almost the same as a dimension in the lateral direction X of the rear waist area 14 in a natural state (state in which all elastic members are not elongated).

Referring again to FIG. 9, in the worn state, the pocket side areas 32 rise by the belt area 23 being contracted in the lateral direction X due to the contractile force of the upper rear waist elastic members 64, and by the pocket inner area 42 being spaced apart from the middle part of the belt area 23, the pocket space S larger than the pocket space of the diaper 10 of the first embodiment is defined.

Figure 11:
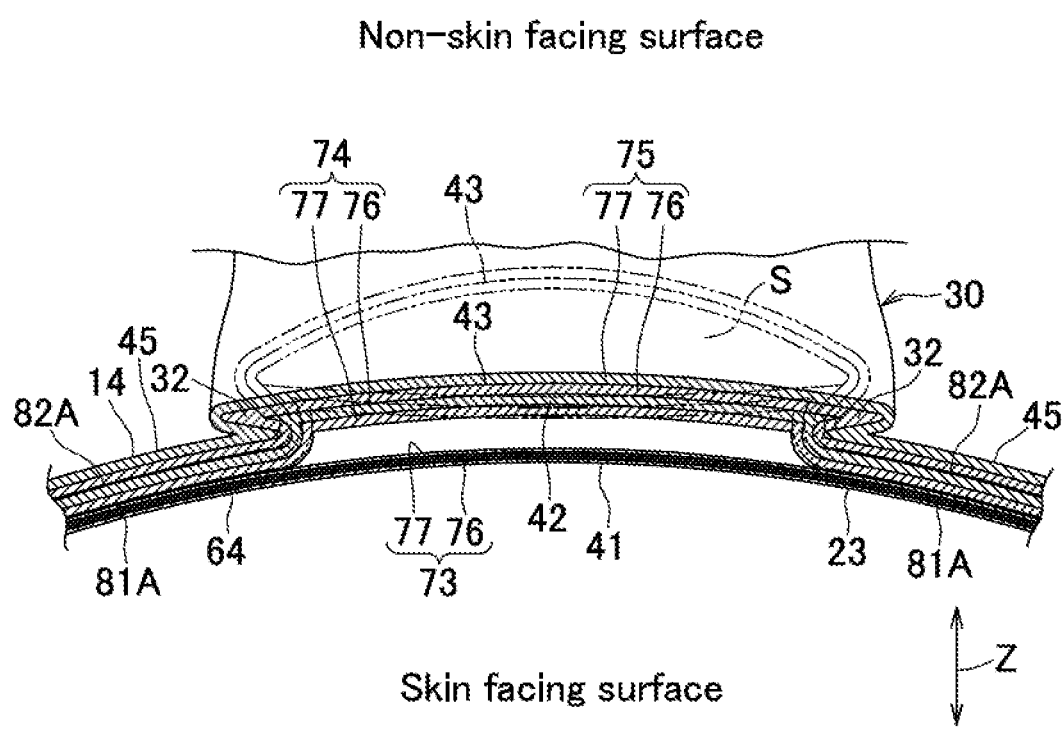
FIG. 11 is a diagram of the rear waist region of the diaper in an unworn state and a worn state, viewed from the top.

In the diaper 10 according to the present embodiment, since the pocket 30 includes the pocket inner and outer areas 42, 43, and the pocket side areas 32, it has a solid (three-dimensional) shape even in an unworn state, as the unworn state is shown by solid lines in FIG. 11, and the worn state is shown by virtual lines in FIG. 11, it is possible to form intentionally in any state the pocket space S capable of collecting and containing the body exudates temporarily.

Moreover, even when the wearer is in a supine state, and a body pressure of the wearer is exerted to the pocket 30, since the pocket side areas 32 are in tucked-in form and the pocket inner area 42 and the middle part 41 of the belt area 23 come in contact with each other, it may not create a discomfort against the wearer, due to a partial thickness change in the rear waist region 14 by the base sheet 70 being deformed to be distorted by the body pressure. Since the pocket side areas 32 can be folded and stretched in the thickness direction Z, when released from the body pressure, the pocket side areas 32 rise in a direction away from the body, and the solid (three-dimensional) pocket space S is formed again.

The diaper 10 has the upper waist elastic members 64 extending between the both side edges 14c of the rear waist region 14. Accordingly, even in the case where a force pressing the pocket 30 against the body side is exerted repeatedly, such as the case where the wearer is in a supine state, or the case where mother holds the baby by putting arms around baby's back, since the pocket 30 can repeatedly assumes a solid (three-dimensional) shape stably by bending and stretching movement of the pocket side areas 32, even in a case of wearing by a few-month-old baby changing the posture frequently and repeatedly passing loose stools quite frequently, it is possible to collect the loose stool assuredly in the pocket space S. Moreover, in the present embodiment, as mentioned already, since the pocket inner area 42, having the required dimension in the vertical direction Y, may function as a top surface of the pocket 30 by moving rearward upon being inclined with respect to the middle part 41 by the pocket side areas 32 being erected, it is possible to collect even larger amount of body exudates as compared to a type without a folding structure of both side areas of the pocket and the top surface.

In the worn state, when the belt area 23 is elongated in the lateral direction X (direction of waist) to the extent such that gathers by contraction effect of the upper rear waist elastic members 64 disappear, the folds in the pocket side areas 32 are released and the pocket inner area 42 may move toward the middle part 41 and the pocket space S may disappear. Consequently, even when the belt area 23 is elongated in the lateral direction X, since the pocket 30 assumes the solid (three-dimensional) shape, it is preferable that an amount of contraction in the lateral direction X of the belt area 23 including the middle part 41 (a length of the contracted portion in the lateral direction X) is larger than an amount of contraction of the pocket inner area 42 and/or the pocket outer area 43 in the lateral direction X. In this case, even when the belt area 23 is elongated by a predetermined multiplying factor in the lateral direction X compared to the natural state (at the time of contraction) for instance, the pocket side areas 32 are not reclined completely, and the pocket 30 can maintain the solid (three-dimensional) shape.

Accordingly, it is preferable to dispose elastic members stretchable in the lateral direction X in the belt area 23 on one hand, and not to dispose elastic members in the pocket inner area 42 and/or the pocket outer area 43 on the other hand, and to let it to be practically unstretchable elastically. Moreover, although it is not shown in the diagram, for disposing elastic members stretchable in the lateral direction X in the pocket inner area 42 and/or the pocket outer area 43, it is preferable to dispose elastic members having a coefficient of contraction lower than that for elastic members disposed in the central portion, or in other words, the upper rear waist elastic members 64. In the case where the elastic members stretchable in the lateral direction X are disposed in the pocket inner area 42, when a force acting to recline the pocket side areas 32 is exerted to the pocket side areas 32 by the middle part 41 being elongated, since the elastic members are not contracted and, an erected state of the pocket side areas 32 and a state of the pocket inner area 42 spaced apart from the middle part are maintained against the contractive force, the pocket 30 can assume the solid (three-dimensional) shape stably. Furthermore, in a case in which, both the pocket inner and outer areas 42, 43 have elastic stretchability, for forming the pocket 30 stably, it is preferable that a coefficient of contraction in the lateral direction X of the pocket inner area 42 is higher than a coefficient of contraction in the lateral direction X of the pocket outer area 43.

Modified Example 1

Figure 12:
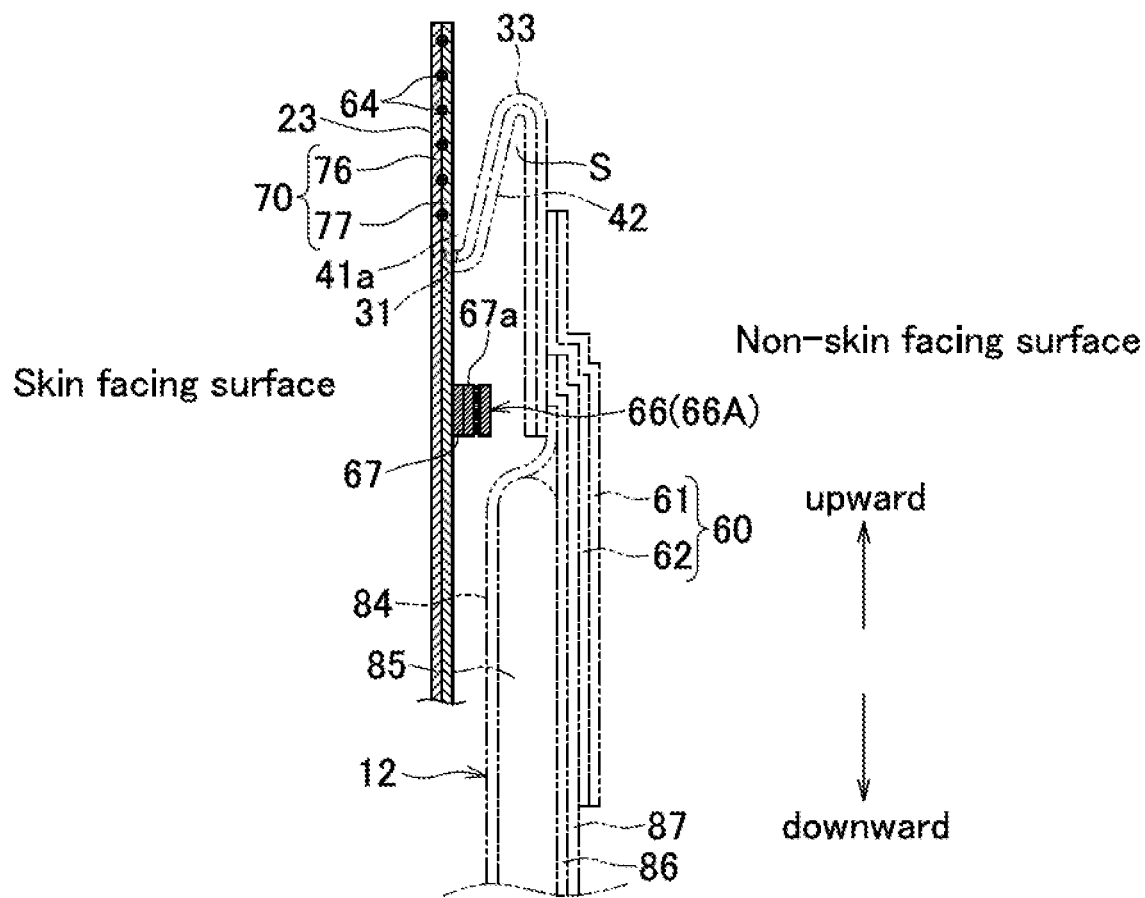
FIG. 12 is a cross-sectional view similar to FIG. 7 of a modified example 1.

FIG. 12 shows a modified example 1 of the diaper 10 according to the first and second embodiments. In the diaper 10, upper ends 67a of the pair of tape fasteners 66 are positioned at a lower side of the folding part 31 which is the lower end of the pocket inner area 24, in the vertical direction Y. Therefore, when the two tape fasteners 66 are connected, it is possible to make large a space between the pocket inner area 42 and the pocket outer area 43 in the direction of thickness. Consequently, at disposal of the diaper 10, it is possible to prevent assuredly the body exudates inside the pocket 30 from leaking.

Modified Example 2

Figure 13:
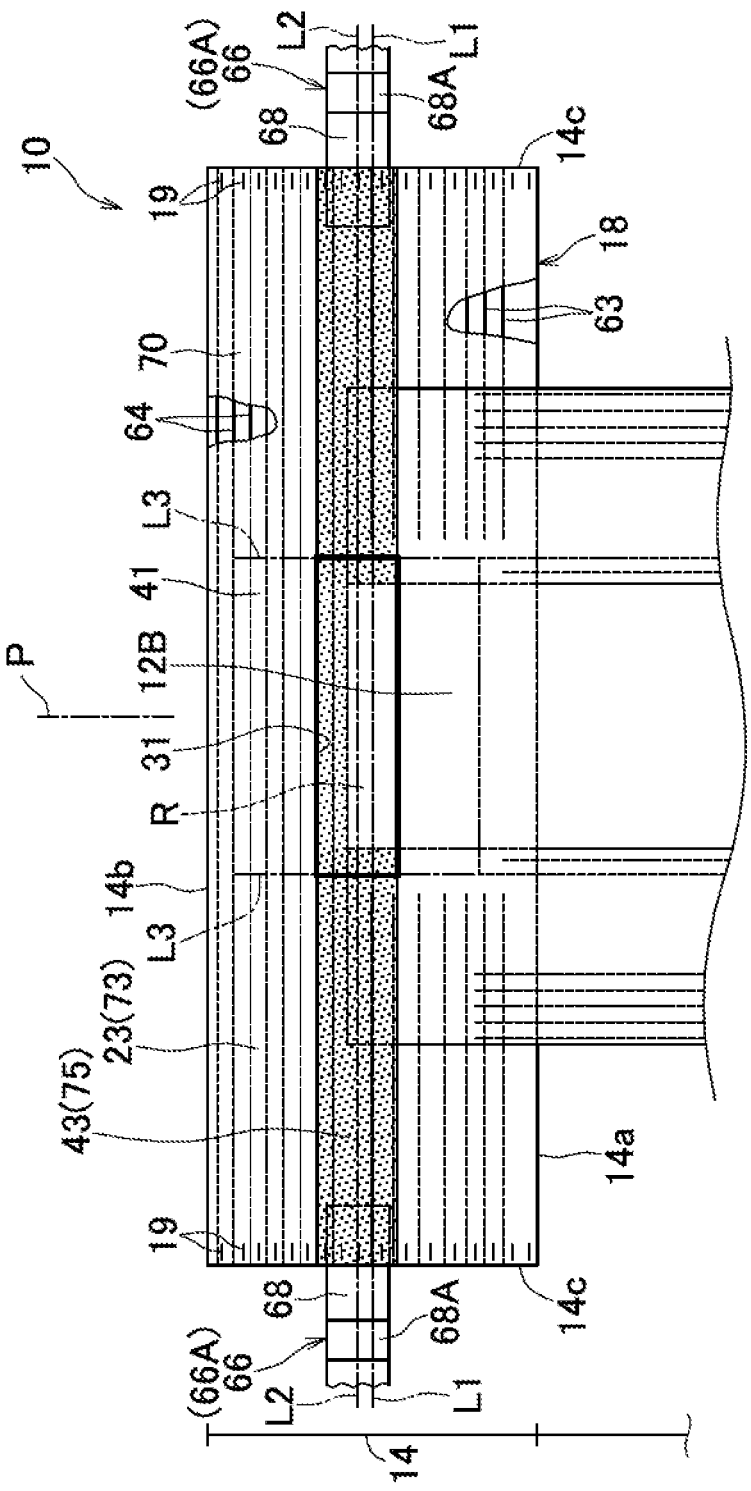
FIG. 13 is a cross-sectional view similar to FIG. 4 of a modified example 2.

FIG. 13 shows a modified example 2 of the diaper 10 according to the first and second embodiments. Referring to FIG. 13, the rear waist region 14 of the diaper 10 has the first virtual line L1 bisecting a dimension of the rear waist region in the vertical direction Y. The tape fastener 66 has a second virtual line L2 bisecting a dimension of the tape fastener 66 in the vertical direction Y, and the tape fastener 66 is fixed (attached) to the rear waist region 14 such that the second virtual line L2 is positioned at an upper side of the first virtual line L1. According to the diaper 10, at disposal of the diaper 10, by overlapping the crotch region 15 with one of the front waist region 13 and the rear waist region 14, and thereafter, connecting the tape fasteners 66, since it is possible to connect the tape fasteners 66 on the waist opening 21 side of the front and rear waist regions 13, 14, it is possible to prevent the body exudates from leaking from the waist opening 21 and to roll-up the diaper 10 compactly at disposal.

Figure 14:
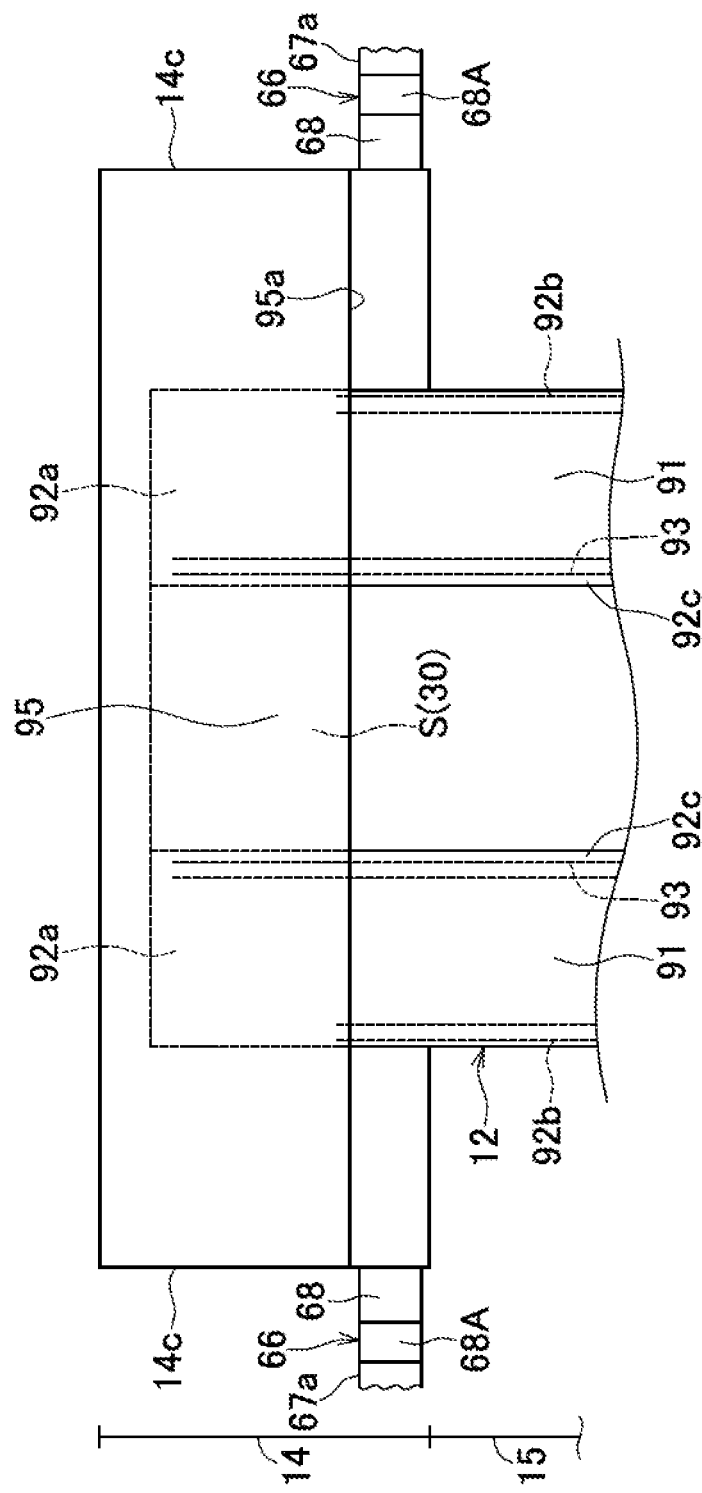
FIG. 14 is a partially enlarged view similar to FIG. 4 of the disposable wearing article (diaper) according to the second embodiment of the present invention.

A diagram similar to FIG. 4 of the second embodiment of the disposable wearing article (diaper) according to the present invention is shown in FIG. 14. The absorbent chassis 12 of the diaper 10 includes a pair of barrier cuff sheets 91 extending in the vertical direction Y and separated apart in the lateral direction X, and a skin contact sheet 95 positioned on the skin facing surface of the barrier cuff sheets 91. Moreover, the tape fasteners 66 are attached to the rear waist region 14 such that the upper end 67a thereof is at a lower side of a lower end 95a of the skin contact sheet 95. In FIG. 14, the waist elastic members are omitted for the sake of expediency.

The skin contact sheet 95 is a sheet defining the belt area 23, positioned between both side edges 14c of the rear waist region 14, and is made of fibrous nonwoven fabrics.

The pair of barrier cuff sheets 91 is folded inward of the lateral direction, and have inner surfaces fixed to each other. The pair of barrier cuff sheets 91 includes front fixing part and rear fixing parts 92a opposed to each other to be separated apart in the vertical direction Y, and fixed to a skin facing surface of the body side liner 84, fixing side edges 92b extending in the vertical direction Y, opposed to each other to be separated apart outboard of the lateral direction X, and fixed to the skin facing surface of the body side liner 84, and free side edges 92c positioned at an inner side of the lateral direction X from the fixing side edges 92b. The skin contact sheet 95 is attached to a skin facing surface of the free side edges 92c of the barrier cuff sheet 91 on one hand, and in the lateral direction X, between the free side edges 92c, is not attached to the barrier cuff sheets 91 on the other hand. Cuff elastic members 93 extending in the vertical direction Y, made of string- or strap-like elastic members are fixed contractively in an elongated state at an interior of the free side edges 92c. By the cuff elastic members 93 being contracted in the vertical direction Y, the free side edges 92c move (are separated) away from the body side liner 84 toward the wearer's body, and a pair of barrier cuffs for preventing lateral leakage of the body exudates is formed.

Figure 15:
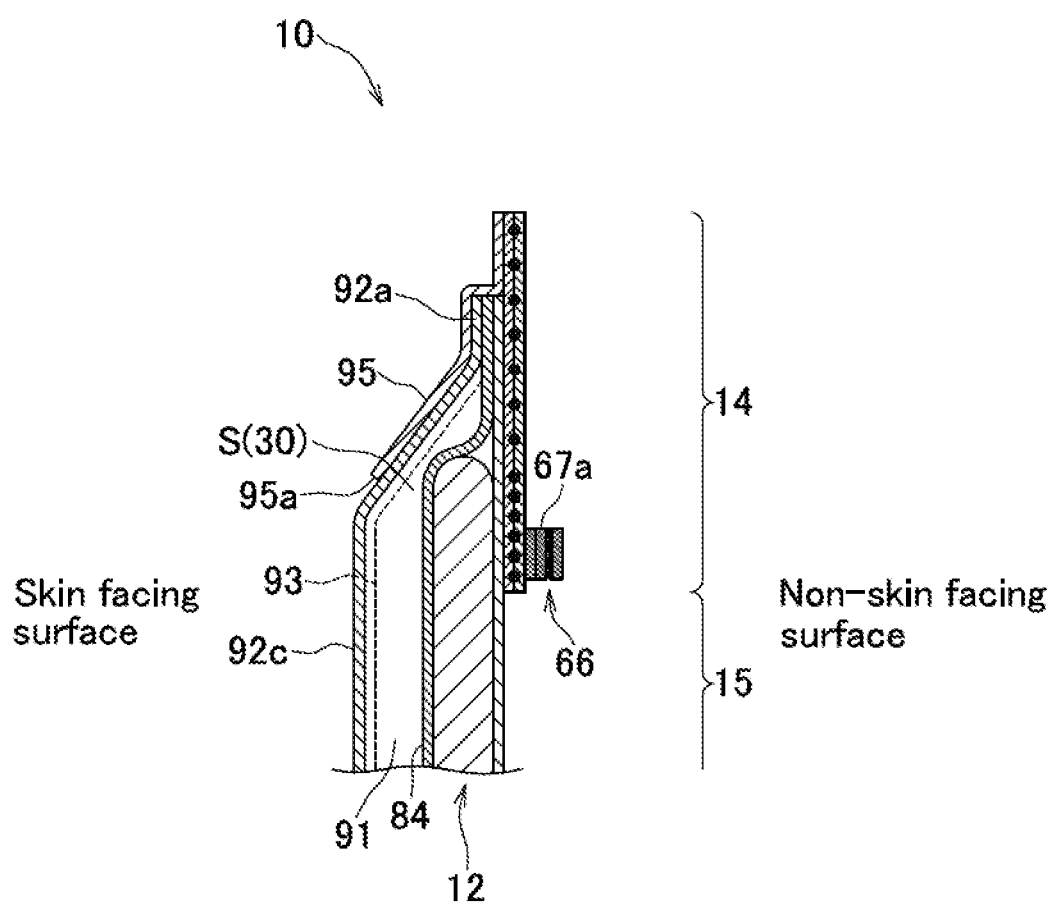
FIG. 15 is a vertical cross-sectional view of the diaper according to the second embodiment in a worn state.

At the time of wearing the diaper 10, as the cuff elastic members 93 are contracted, the free side edges 92c space away from the body side liner 84 as shown in FIG. 15, and accordingly, the pocket space S for collecting and containing the body exudates is formed between the body side liner 84 and the skin contact sheet 95, in the thickness direction Z.

The pocket 30 of the present invention is a pocket positioned on the skin facing surface, in which the pocket space S for collecting and containing the body exudates is formed between a sheet forming the belt area 23 and a sheet positioned on the non-skin facing surface of the sheet forming the belt area 23, includes diapers having different structures, not to mention the pocket 30 of the first embodiment and the pocket 30 of the second embodiment.

For each of the constituent materials forming the diaper 10, various known materials generally used in this type of field may be used without restriction unless mentioned in particular. Moreover, the terms such as 'the first', 'the second', and 'the third' used in the present description are used simply for distinguishing similar components and positions. Furthermore, when the wearer is in a side-lying state, an upper side of the diaper 10 is a side close to the head of the wearer, and a lower side of the diaper 10 is a side close to the legs of the wearer.

Moreover, in the embodiments described above, disposable wearing articles in which the tape fasteners 66 are attached to the rear waist region 14 of the diaper 10 are described. However, the present invention is not restricted to the disposable wearing articles having the abovementioned structure, and the tape fasteners 66 may be attached to the front waist region 13.

The invention claimed is:

1. A disposable wearing article having a vertical direction and a lateral direction, and a skin facing surface and a non-skin facing surface on an opposite side thereof, said disposable wearing article comprising:
   a front waist region;
   a rear waist region;
   a crotch region positioned between the front waist region and the rear waist region; and
   a pair of leg openings, and a waist opening defined by side edges of the front waist region and the rear waist region being connected,
   wherein
   at least one of the front waist region and the rear waist region includes a pair of tape fasteners fixed to the non-skin facing surface of the side edges,
   at least one of the front waist region and the rear waist region includes a pocket openable toward the crotch region, on the skin facing surface, an upper end of a fixing part of each tape fastener in the pair of tape fasteners is positioned at a lower side of a closing edge positioned on the waist opening side of the pocket in the vertical direction, at least one of the front waist region and the rear waist region has a belt-shaped area positioned on the skin facing surface and extending in the lateral direction, the pocket is positioned on the non-skin facing surface, facing the belt-shaped area in a direction of thickness, at a middle part in the lateral direction, the pocket includes
- a pocket outer area extending from a side of the crotch region toward a side of the waist opening, and
- a pocket inner area facing the pocket outer area and the belt-shaped area in the direction of thickness, continuous with the pocket outer area, and connected to the belt-shaped area, the upper end of the fixing part of each tape fastener in the pair of tape fasteners is positioned at a lower side of an upper end of the pocket outer area in the vertical direction, and the upper end of the fixing part of each tape fastener in the pair of tape fasteners is either positioned at a lower side of a lower end of the pocket inner area in the vertical direction, or coinciding with the lower end of the pocket inner area in the vertical direction.

2. The disposable wearing article according to claim 1, wherein the upper end of the fixing part of each tape fastener in the pair of tape fasteners and the lower end of the pocket inner area coincide with each other in the vertical direction.

3. The disposable wearing article according to claim 1, wherein
the front waist region and the rear waist region have a first virtual line bisecting a dimension of the front waist region and the rear waist region in the vertical direction, and each tape fastener in the pair of tape fasteners has a second virtual line bisecting a dimension of the tape fastener in the vertical direction, and each tape fastener in the pair of tape fasteners is fixed to any one of the front waist region and the rear waist region such that the second virtual line is positioned at an upper side of the first virtual line.

4. The disposable wearing article according to claim 1, wherein the pocket further includes two pocket side areas folded inward in the lateral direction.

5. The disposable wearing article according claim 1, wherein
each tape fastener in the pair of tape fasteners has
- a base part formed of fibrous nonwoven fabrics, the fixing part positioned at one end of the base part and fixed to the non-skin facing surface of the rear waist region, and
- a free part positioned at the other end of the base part and extending outboard of the front waist region and the rear waist region in the lateral direction, and the free part has a fastening area that is configured to be fastened to the base part.

* * * * *